United States Patent [19]
Sheen et al.

[11] Patent Number: 5,365,778
[45] Date of Patent: Nov. 22, 1994

[54] METHOD FOR MEASURING LIQUID VISCOSITY AND ULTRASONIC VISCOMETER

[75] Inventors: Shuh-Haw Sheen, Naperville; William P. Lawrence, Downers Grove; Hual-Te Chien, Naperville; Apostolos C. Raptis, Downers Grove, all of Ill.

[73] Assignee: The University of Chicago, Chicago, Ill.

[21] Appl. No.: 188,526

[22] Filed: Jan. 28, 1994

[51] Int. Cl.$^5$ .................. G01N 11/00; G01N 29/02
[52] U.S. Cl. .................................. 73/54.41; 73/32 A
[58] Field of Search .............. 73/54.01, 54.24, 32 A, 73/54.41

[56] References Cited

U.S. PATENT DOCUMENTS 3,903,732  9/1975  Rork et al. .................... 73/54.24

FOREIGN PATENT DOCUMENTS 89564  3/1992  Japan ........................... 73/32 A

OTHER PUBLICATIONS

F. Cohen-Tenoudji et al., "A Shear Wave Rheology Sensor," Mar. 1987, pp. 263–269, *IEEE Transactions on Ultrasonics, Ferroelectronics, and Frequency Control,* vol. UFFC-34, No. 2.

Sheen et al., "Advanced Research in Instrumentation and Control Technology;" Proceeding of 1990—Conf-900-981 [DE91009344].

*Primary Examiner*—Hezron E. Williams
*Assistant Examiner*—Joseph W. Roskos
*Attorney, Agent, or Firm*—Mason, Kolehmainen, Rathburn & Wyss

[57] ABSTRACT

An ultrasonic viscometer and method for measuring fluid viscosity are provided. Ultrasonic shear and longitudinal waves are generated and coupled to the fluid. Reflections from the generated ultrasonic shear and longitudinal waves are detected. Phase velocity of the fluid is determined responsive to the detected ultrasonic longitudinal waves reflections. Viscosity of the fluid is determined responsive to the detected ultrasonic shear waves reflections. Unique features of the ultrasonic viscometer include the use of a two-interface fluid and air transducer wedge to measure relative signal change and to enable self calibration and the use of a ratio of reflection coefficients for two different frequencies to compensate for environmental changes, such as temperature.

14 Claims, 5 Drawing Sheets

METHOD FOR MEASURING LIQUID VISCOSITY AND ULTRASONIC VISCOMETER

CONTRACTUAL ORIGIN OF THE INVENTION

The United States Government has rights in this invention pursuant to Contract No. W-31-109-ENG-38 between the United States Government and Argonne National Laboratory.

BACKGROUND OF THE INVENTION

1. Field of the Invention

The present invention relates to an apparatus installed non-intrusively and directly to a process stream for measuring fluid viscosity and density.

2. Description of the Prior Art

A need exists for effective instrumentation and diagnostic technology for coal combustion, pyrolysis, and cleanup processes. Control instruments are needed for monitoring specific process parameters such as, viscosity, temperature and flow rate. An on-line viscometer can be used for real-time coal-slurry process control, for example, in the control of slurry viscosity at the slurry atomization step of a combustion process. Furthermore, accurate measurement of slurry viscosity can also ensure efficient and safe operation of other process equipment, such as pumps, valves and nozzles.

Rheological properties of a coal slurry determine most engineering design requirements of a coal process in which a slurry is used. For example, the flow pattern of a coal-slurry in a pipe is related to the shear viscosity of the slurry or to the flow consistency number and flow behavior index when the slurry behaves as a non-Newtonian fluid. A dilute coal/water slurry that is less than 15% by weight can be considered a Newtonian fluid, but higher concentration slurries display non-Newtonian behavior. The apparent viscosity of such a non-Newtonian slurry is dependent on shear rate. In a coal combustion process, the coal slurry is typically under high shear rate at the injection nozzle of the slurry atomizer. There is increasing evidence that the size of the slurry drops at the exit of the atomizer strongly depends on slurry viscosity or rheological properties. It would therefore be of great value to the control of atomization if slurry viscosity could be measured at the atomizer.

It is an object of the present invention to provide an improved method and apparatus for measuring fluid or liquid viscosity.

It is an object of the present invention to provide an improved method and ultrasonic viscometer for measuring liquid viscosity.

SUMMARY OF THE INVENTION

In brief, these and other objects and advantages of the invention are provided by an ultrasonic viscometer and method for measuring fluid viscosity. Ultrasonic shear and longitudinal waves are generated and coupled to the fluid. Reflections from the generated ultrasonic shear and longitudinal waves are detected. Phase velocity of the fluid is determined responsive to the detected ultrasonic longitudinal waves reflections. Viscosity of the fluid is determined responsive to the detected ultrasonic shear waves reflections. Unique features of the invention include the use of a two-interface fluid and air transducer wedge to measure relative signal change and to enable self calibration and the use of a ratio of reflection coefficients for two different frequencies to compensate for environmental changes, such as temperature.

BRIEF DESCRIPTION OF THE DRAWING

These and other objects and advantages of the present invention will become readily apparent upon consideration of the following detailed description and attached drawing, wherein.

DETAILED DESCRIPTION OF THE PREFERRED EMBODIMENT

Figure 1:
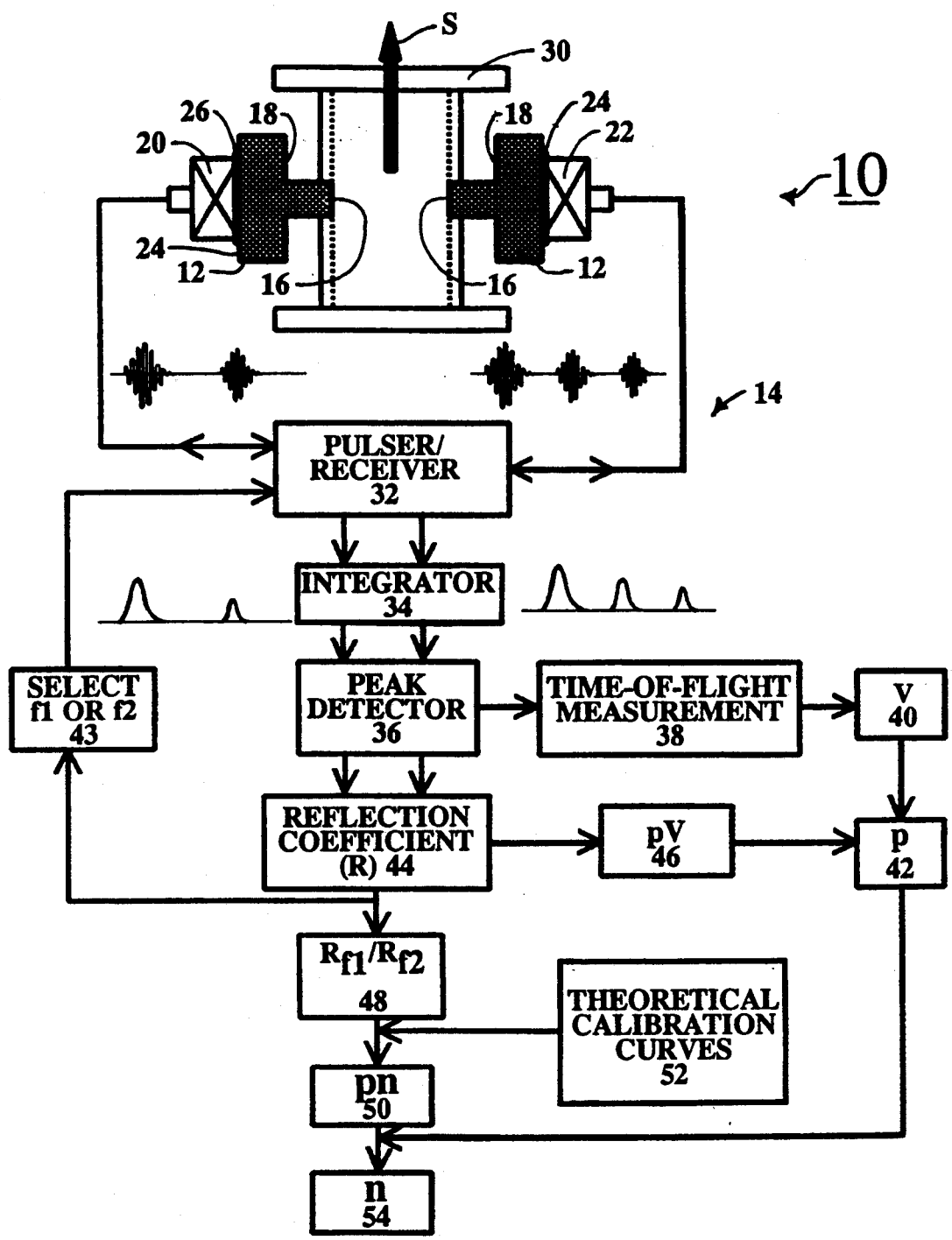
FIG. 1 is a schematic block diagram representation of an ultrasonic viscometer in accordance with the invention.
Figure 2:
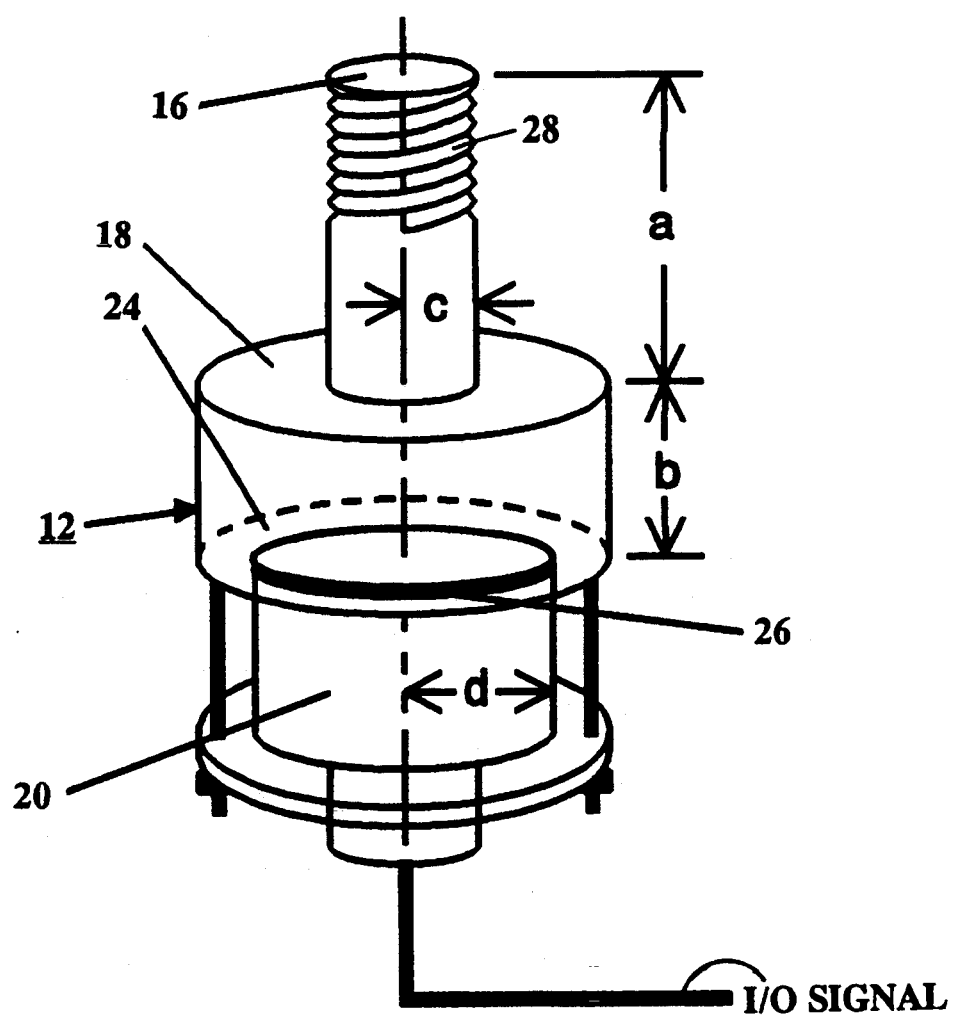
FIG. 2 is a perspective view of a transducer wedge of the ultrasonic viscometer of FIG. 1.

Referring to FIGS. 1 and 2, there is shown an ultrasonic apparatus for monitoring fluid viscosity of single phase or multiphase flows in accordance with the invention and generally designated by the reference character 10. Viscometer 10 differs from conventional viscometers in its nonintrusive and in-process/real-time capabilities which are important for many industrial applications. Viscometer 10 includes a pair of transducer wedges 12 for direct coupling to the fluid being monitored and circuitry generally designated by 14 for conditioning and processing the detected signal. Shear and longitudinal waves are generated in a respective one of the wedges 12 and provide data for several process parameters, such as, density, sound speed, temperature, flow rate and the viscosity measurement.

Ultrasonic viscometer 10 can be used for on-line monitoring of rheological properties of coal slurries. As illustrated in FIGS. 1 and 2 of the drawing, the transducer wedge 12 includes a pair of spaced-apart, parallel surfaces 16 and 18 with one surface 16 for direct contact with the fluid and the other surface 18 for contact with air. During operation, the interface 16 is in contact with the monitored fluid within a process stream indicated by an arrow labelled S. The other interface 18 is in contact with the air. The air interface 18 causes a total reflection of the incident ultrasonic wave, thus the reflection acts as the reference signal that is used to measure the relative changes of the other reflection from the fluid interface 16. An advantage is that the two interface arrangement provides a differential measurement which reduces the errors introduced by other process parameters such as temperature and flow rate.

Ultrasonic viscometer 10 includes a shear transducer 20 and a longitudinal transducer 22 mounted to a respective one of the wedges 12. A respective one of the longitudinal transducer 22 and shear transducer 20 is mounted on an opposed side 24 of the wedge air interface 18. A coupling material 26, for example, such as epoxy or gold foil, couples the transducers 20 and 22 to the mounting surface 24. Transducer wedges 12 can be formed of various materials, such as, aluminum, stainless steel, brass, titanium, fused quartz or copper. Each transducer wedge 12 preferably is formed of aluminum which provides good sensitivity and also is relatively inexpensive and easily formed or machined. Transducer wedge 12 includes a threaded surface 28 for connection with a mounting flanged member 30 containing the process stream S. As shown in FIG. 2, the transducer wedges 12 are arranged as defined by the following equations.

a=(n+¼)*lambda$_S$ (or *lambda$_L$ for the longitudinal transducer 22)
b=m*lambda$_S$ (or *lambda$_L$ for the transducer 22)
c=0.71d
d=Transducer radius where m, n=integers and the selection of b depends on process temperature.

A compressional wave is sent out by the transducer 22 and reflected back at the wedge/fluid boundary 16. In accordance with the invention, the reflection coefficient is calculated and related to the acoustic impedance of the fluid which is a product of density and sound speed.

The acoustic impedance pV of a liquid is determined from measurement of the reflection coefficient, $R_L$, for the longitudinal waves at a solid-liquid interface and is related to the coefficient by the equation:

$$R_L=(Z_L-Z_W)/(Z_L+Z_W)$$

where V is the phase velocity of the medium, $Z_L$=pV the acoustic impedance of the liquid and $Z_W$ is the acoustic impedance of the solid wedge. The shear viscosity, n, is given by:

$$n=C(1-R_S)^2/(1+R_S)^2$$

where $R_S$ is the reflection coefficient of the shear wave and C is a wedge constant.

A pulser/receiver 32 generates a pulse signal applied to the transducers 20 and 22 to create a local fluid disturbance and receives the reflected signal corresponding to the disturbance decay. A selected frequency of, for example, 0.5 or 1 MHz is applied to the longitudinal transducer 22. A selected frequency of, for example, 1 or 5 MHz is applied to the shear transducer 20.

Reflected bursts are applied to an integrator 34 and are integrated. Their peak amplitudes and times of flight are measured at a first block 36 labelled PEAK DETECTOR and a second block 38 labelled TIME-OF-FLIGHT MEASUREMENT, respectively.

The longitudinal waves are used to determine the phase velocity at a block 40 labelled V and density of the fluid at a block 42 labelled p.

The shear waves reflection coefficients $R_S$ identified at a block 44 are used to determine the product of fluid density and viscosity at a block 46. The ratio of the two measurements gives the fluid density at block 42. A first or second frequency f1 or f2 is selected at a block 43 and applied to the pulser/receiver block 32.

Since the dependence on frequency is nonlinear, the difference or the ratio of the reflection coefficients for two different frequencies advantageously is used at a block 48 to provide a quantitative measurement of the density-viscosity product as indicated at a block 50. To obtain the fluid viscosity one needs to know the fluid density which can be arrived at by measuring the longitudinal-wave phase velocity in the fluid and its reflection coefficient at the fluid-wedge interface. Theoretical calibration curves indicated at a block 52 can be combined with the ratio of reflection coefficients provided by block 48. The ultrasonic viscometer determines or measures the fluid viscosity and density separately at blocks 54 and 42, respectively.

Various commercially available devices can be used for the transducers 20 and 22, for example, such as, part Number V103 and part Number V155, manufactured and sold by Panametrics of Walham, Mass. A pulser/receive model number Panametrics 5052 UA manufactured and sold by Panametrics of Walham, Mass. can be used for the pulser-receiver 32.

FIGS. 3-8 illustrate the operation of the ultrasonic viscometer 10 with transducer wedges 12 formed of aluminum and an angle theta of zero degrees of the parallel surfaces 16 relative to the fluid process stream S.

Figure 3:
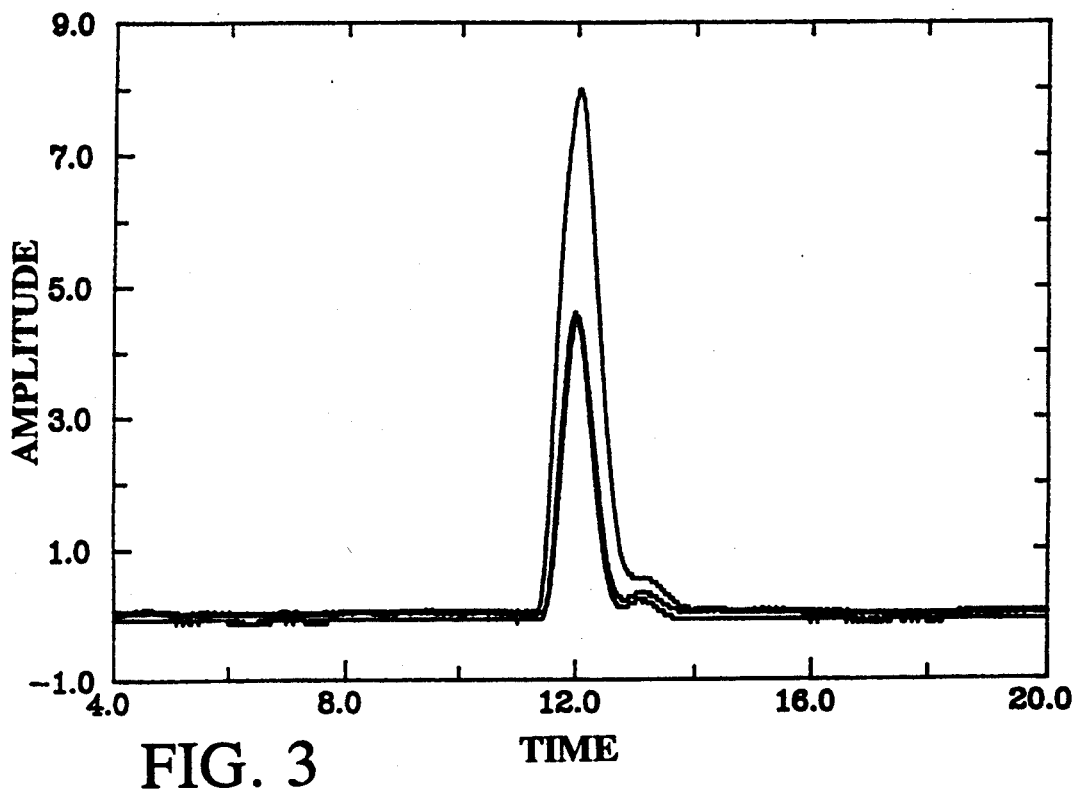
FIGS. 3–8 are graphs illustrating the operation of the ultrasonic viscometer of FIG. 1.

FIG. 3 shows amplitude (volts) versus time (microseconds) for typical reflected pulses obtained with a longitudinal transducer from air, asphalt T-300 and asphalt T-750. The higher amplitude reflected pulse is from air and the lower amplitude substantially coincident pulses are from asphalt T-300 and asphalt T-750.

Figure 4:
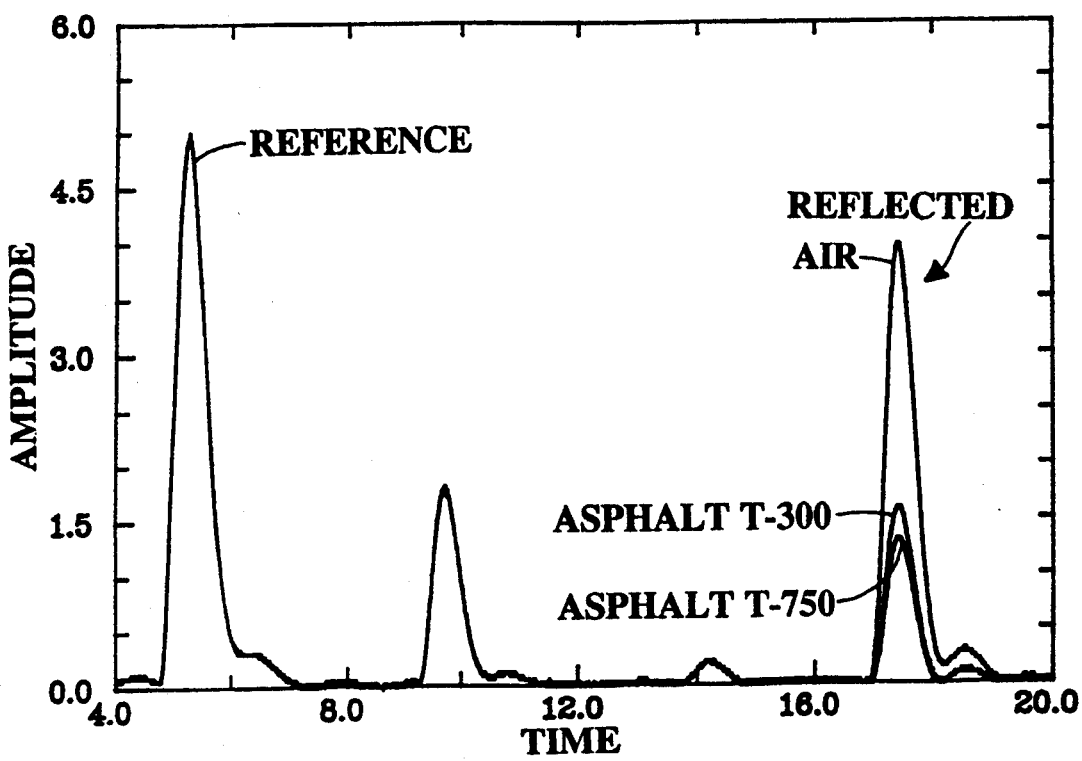

FIG. 4 shows amplitude (volts) versus time (microseconds) for typical pulses obtained with a shear transducer from air, asphalt T-300 and asphalt T-750. The air-solid reflection on the left labelled REFERENCE is used as the reference signal, because the total reflection is expected to come from the air-solid interface 18. The pulses on the right labelled REFLECTED correspond to the reflection from the liquid-solid interface 16.

Figure 5:
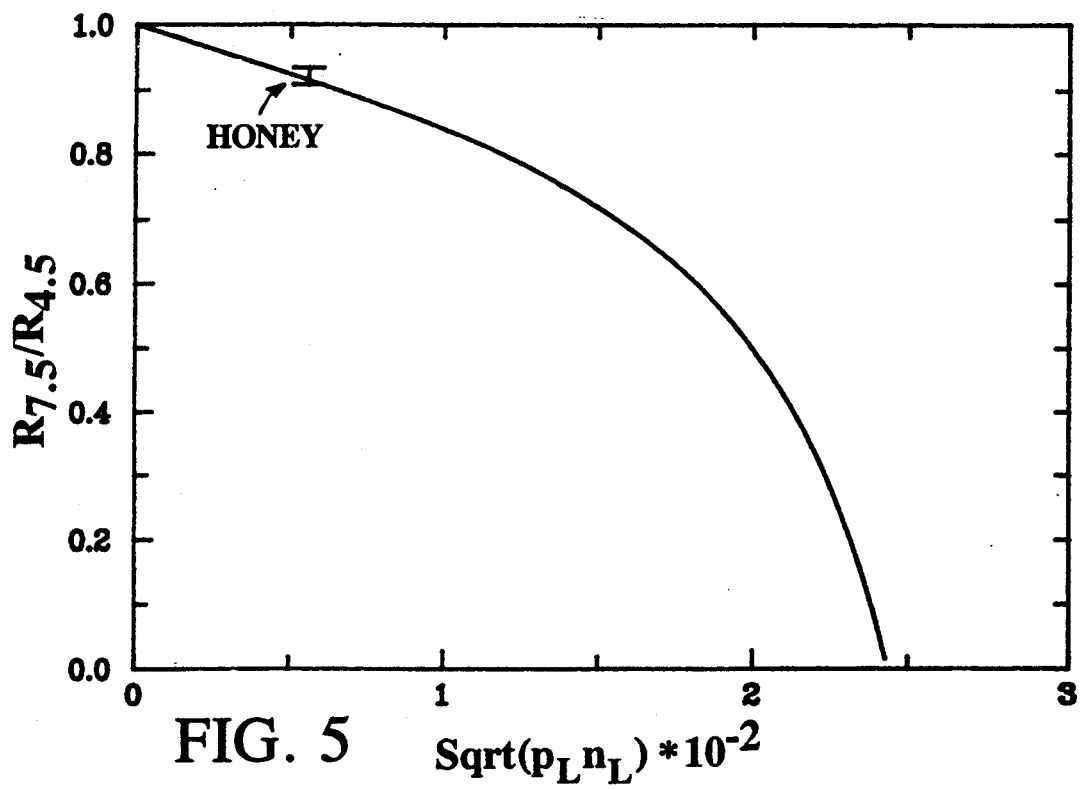

FIG. 5 shows the ratio of the reflection coefficients for two different frequencies of 7.5 MHz and 4.5 MHz versus the square root of density-viscosity product times $10^{-2}$ (g/cm$^3$ poise). A viscosity data point for honey is shown.

Figure 6:
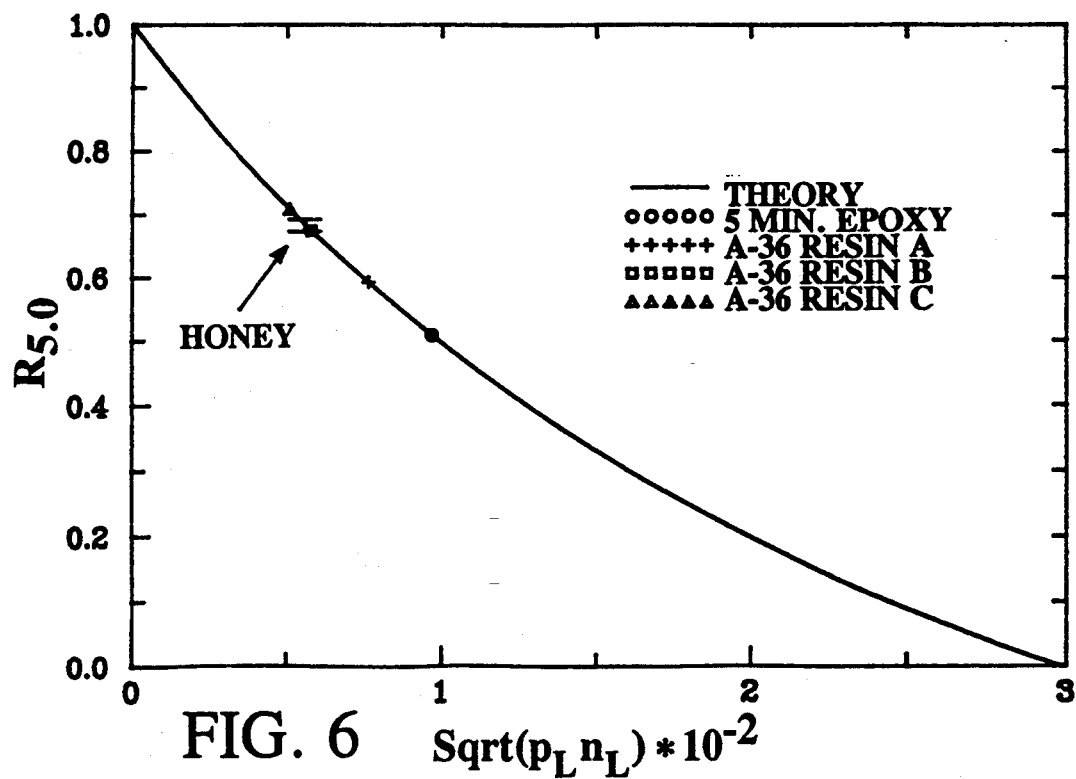

FIG. 6 shows the reflection coefficients of the test liquids including honey, 5-minute epoxy, A-36 resin a, A-36 resin b and A-36 resin c measured at 5 MHz. The solid line in FIG. 6 represents the calculated reflection coefficients.

Figure 7:
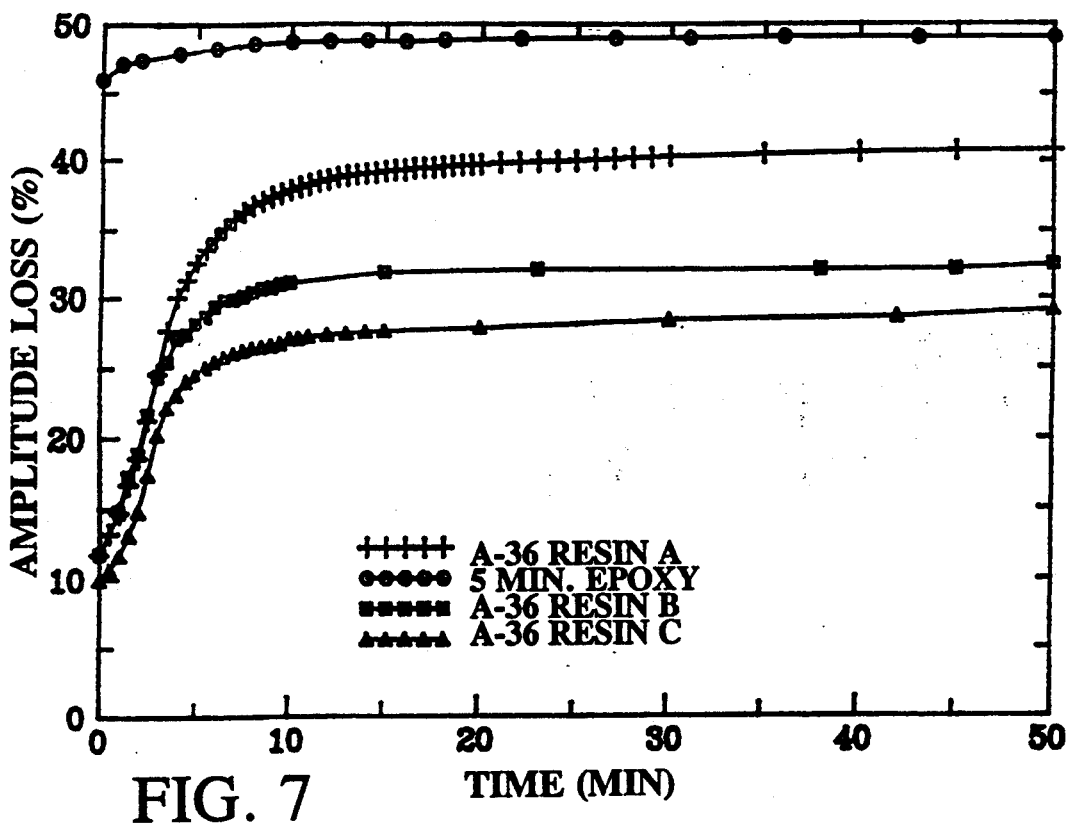

FIG. 7 shows the normalized reflection amplitude loss versus time (minutes) during the curing process of a five-minute epoxy and three epoxy resins A, B and C.

Figure 8:
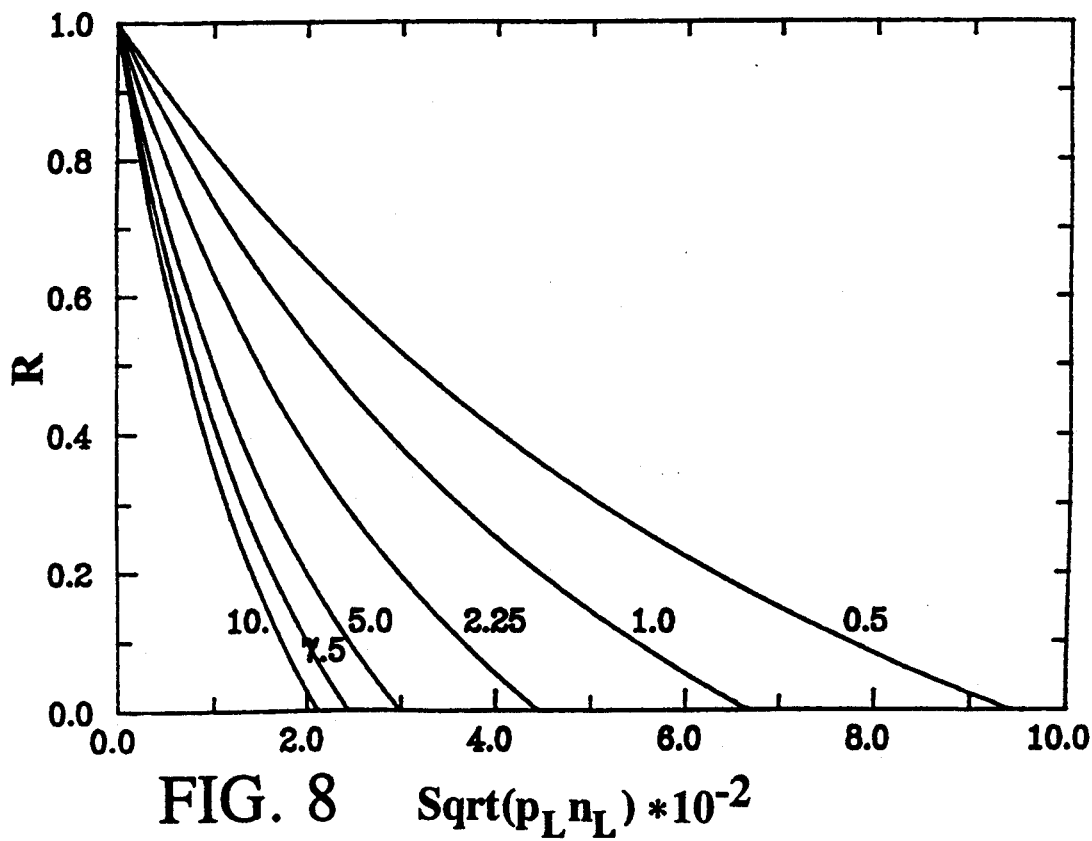

FIG. 8 shows the reflection coefficient for six different frequencies of 10 MHz, 7.5 MHz, 5.0 MHz, 2.25 MHz, 1 MHz and 0.5 MHz versus the square root of density-viscosity product (g/cm$^3$ poise).

Obviously, many modifications and variations of the present invention are possible in light of the above teachings. Thus, it is to be understood that, within the scope of the appended claims, the invention may be practiced otherwise than as specifically described above.

What is claimed and desired to be secured by Letters Patent of the United States is:

1. An ultrasonic viscometer for measuring viscosity of a fluid comprising:
 means for generating ultrasonic shear waves coupled to the fluid;
 means for generating ultrasonic longitudinal waves coupled to the fluid;
 means for detecting reflections from said generated ultrasonic shear waves;
 means for detecting reflections from said generated ultrasonic longitudinal waves;
 means responsive to said ultrasonic longitudinal waves reflections detecting means for determining phase velocity of the fluid; and
 means responsive to said ultrasonic shear waves reflections detecting means for determining viscosity of the fluid.

2. An ultrasonic viscometer as recited in claim 1 wherein said means responsive to said ultrasonic longitudinal waves reflections detecting means for determining phase velocity of the fluid include means for determining density of the fluid.

3. An ultrasonic viscometer as recited in claim 1 wherein said means responsive to said ultrasonic shear waves reflections detecting means for determining viscosity of the fluid include means for determining density of the fluid.

4. An ultrasonic viscometer as recited in claim 1 wherein said means for generating ultrasonic shear and longitudinal waves include means for selecting between a first frequency and a second frequency.

5. An ultrasonic viscometer as recited in claim 1 further includes means for measuring time-of-flight between reflected peaks and means responsive to said time-of-flight measuring means for calculating a phase velocity of the fluid.

6. An ultrasonic viscometer as recited in claim 1 wherein said means for generating ultrasonic shear and longitudinal waves include a transducer wedge having a fluid interface surface in contact with the fluid and an air interface surface in contact with air.

7. An ultrasonic viscometer as recited in claim 6 wherein said air interface surface causes a total reflection of the incident ultrasonic wave providing a reflection reference signal.

8. An ultrasonic viscometer as recited in claim 6 wherein said transducer wedge is formed of aluminum.

9. A method for measuring viscosity of a fluid comprising the steps of:
   generating ultrasonic shear waves coupled to the fluid;
   generating ultrasonic longitudinal waves coupled to the fluid;
   detecting reflections from said generated ultrasonic shear waves;
   detecting reflections from said generated ultrasonic longitudinal waves;
   determining phase velocity of the fluid responsive to said detected ultrasonic longitudinal waves reflections; and
   determining viscosity of the fluid responsive to said detected ultrasonic shear waves reflections.

10. A method for measuring viscosity of a fluid as recited in claim 9 further includes the step of selecting a first frequency for generating said shear and longitudinal waves.

11. A method for measuring viscosity of a fluid as recited in claim 10 further includes the step of selecting a second frequency for generating said shear and longitudinal waves.

12. A method for measuring viscosity of a fluid as recited in claim 11 further includes the step of calculating a ratio of reflection coefficients for said first and second selected frequencies.

13. A method for measuring viscosity of a fluid as recited in claim 9 further includes the step of determining density of the fluid.

14. An ultrasonic fluid monitoring apparatus comprising:
   first and second transducer wedge means for direct coupling to the fluid being monitored;
   means coupled to said first transducer wedge means for generating ultrasonic shear waves coupled to the fluid;
   means coupled to said second transducer wedge means for generating ultrasonic longitudinal waves coupled to the fluid;
   means for detecting reflections from said generated ultrasonic shear waves;
   means for detecting reflections from said generated ultrasonic longitudinal waves;
   means responsive to said ultrasonic longitudinal waves reflections detecting means for determining phase velocity of the fluid; and
   means responsive to said ultrasonic shear waves reflections detecting means for determining viscosity of the fluid.

* * * * *